United States Patent [19]

Sorbie et al.

[11] Patent Number: 5,030,237
[45] Date of Patent: Jul. 9, 1991

[54] ELBOW PROSTHESIS

[75] Inventors: Charles Sorbie; Gerald A. B. Saunders, both of Kingston, Canada

[73] Assignee: Queen's University at Kingston, Kingston, Canada

[21] Appl. No.: 169,440

[22] Filed: Mar. 17, 1988

Related U.S. Application Data

[63] Continuation-in-part of Ser. No. 730,814, May 6, 1985, abandoned, which is a continuation-in-part of Ser. No. 507,378, Jun. 24, 1983, abandoned.

[51] Int. Cl.$^5$ .................................................. A61F 2/38
[52] U.S. Cl. ....................................................... 623/20
[58] Field of Search ............................... 623/16, 18, 20

[56] References Cited

U.S. PATENT DOCUMENTS

| | | | |
|---|---|---|---|
| 4,242,758 | 1/1981 | Amis | 623/20 |
| 4,436,684 | 3/1984 | White | 623/16 |
| 4,479,271 | 10/1984 | Bolesky et al. | 623/18 |

OTHER PUBLICATIONS

Shiba et al., Journal of Orthopaedic Research, vol. 6, pp. 897-906 (1988).
Pritchard, Clinical Orthopaedics and Related Research, No. 179, pp. 223-230 (1983).
Rosenberg et al., Clinical Orthopaedics and Related Research, No. 187, pp. 154-162 (1984).
Rydholm et al., The Journal of Bone and Joint Surgery, vol. 66-B, No. 5, pp. 737-741 (1984).
Inglis et al., The Journal of Bone and Joint Surgery, vol. 62, pp. 1252-1258 (1980).
Bryon et al., Clinical Orthopaedics and Related Research, No. 166, pp. 188-192 (1982).
Ewald et al., The Journal of Bone and Joint Surgery, vol. 62-A, No. 8, pp. 1259-1263, (1980).
Ewald et al., Clinical Orthopaedics and Related Research, No. 182, pp. 137-142 (1984).
Schlein, Howmedica Catalog No. 2999-9-945, "Technique for Inserting the Schlein Total Elbow", (No date).
Evans et al., J. Biomed. Enqrq., vol. 2, (no page numbers) (1980).
Bayley, Reconstr. Surg. Tranmat., vol. 18, pp. 70-83 (1981).
Gschweml, Archives of Orthopaedic and Traumatic Surgery, vol. 98, pp. 143-146 (1981).
Davis et al., Clinical Orthopaedics, vol. 171, pp. 156-160 (1982).

*Primary Examiner*—David J. Isabella
*Attorney, Agent, or Firm*—Richard J. Hicks

[57] ABSTRACT

An elbow prosthesis having a humeral component which substantially replicates the natural trochlear and capitellum convex bearing surfaces has been generated by computer analysis and may be fabricated by a computer controlled cutting and polishing device or may be made by precision casting from a "best-fit" type generalized series of moulds. The prosthesis may be inserted from the medial side of the elbow after preparing the distal humerus to provide a smooth convex surface which fits closely to an inside concave surface of the prosthetic element. The centroidal longitudinal axis of said convex bearing surfaces is coincident with the centroidal longitudinal axis of the concave surface.

14 Claims, 6 Drawing Sheets

ELBOW PROSTHESIS

CROSS REFERENCE TO RELATED APPLICATIONS

This application is a continuation-in-part of our earlier filed and presently pending U.S. patent application Ser. No. 730,814 filed May 5, 1985, and now abandoned, which in turn is a continuation-in-part of U.S. Ser. No. 507,378 filed June 24, 1983 and now abandoned, the disclosure of which are incorporated herein by reference.

FIELD OF INVENTION

This invention relates to an elbow prosthesis and more particularly to an unconstrained prosthesis.

BACKGROUND OF INVENTION AND PRIOR ART

While the elbow joint is, at first sight, a relatively simple hinge joint for which the surgical replacement should be relatively straightforward, further study shows that this is far from the case. The kinematics and kinetics of the elbow are complex and simple constrained hinge arrangements are too primitive to allow sufficient range of motion and proper transfer of forces between the humerus and ulna. The built-in restrictions of the total elbow replacements often result in loosening of the prosthesis, often within only a year or two of placement, causing considerable pain and discomfort. Unconstrained prostheses have been designed with intramedullary stems and while these are an improvement over the constrained types, torsional restrictions still result in early loosening. Resurfacing prostheses have recently been developed which have the advantage that the elements thereof are only surface or onlay replacements which merely cap the ends of the respective bones and consequently require much less bone removal. Such resurfacing prosthesis include the Amis et al device described in U.S. Pat. No. 4,242,758 issued Jan. 6, 1981. This device emphasizes that the relative dimensions of the portions of the outer surface of the humeral prosthesis which extends across the width of the trochlea and capitellum are of great importance, and the patentees have developed a humeral element replacing the natural articulating surfaces of the trochlea and capitellum which has a simplified form based upon three spherical surface portions, the first and second of which articulate with the ulna or a prosthetic device thereon and the second of which, located between the first and third surfaces, articulates with the radius or a prosthetic device thereon. While this device is an improvement over previously developed prostheses, it is still only a very rough approximation or simplification of the actual natural shape of the elbow. This means that not only is there undue stress or pressure on the interface between the metal and bone and also unnatural stresses are placed upon the musculature, ligaments and tendons which may cause pain or, over a period of time, distortion of the natural function of the joint. It is, therefore, believed that nothing short of an exact replication of the natural surfaces of the humerus, ulna and radius is required to provide a satisfactory elbow replacement. The problem is, of course, that the natural end surfaces of these bones are not simple geometric shapes and have never before measured with sufficient accuracy and precision to enable a metal replica thereof to be fabricated by known metal working techniques. While it is, of course, a simple matter to take a wax impression of a bone end and produce an investment casting therefrom, this presupposes that the bone selected is in fact representative of all humeral bones or that all human humerae are identical. As neither of these suppositions is likely to be correct, it was deemed essential to document and average, from many elbows, the surface geometry of the distal end of the humerus and proximal end of the ulna and the extent of cartilage coverage, to test the assumption of an axisymmetric shape, to determine the relationship of axes of symmetry to identifiable bony landmarks and to determine those factors of alignment and geometry underlying the carrying angle.

When this has been achieved it is possible to generate, by computer-aided milling equipment, an unlimited series of standardized elbow prostheses. We have found that a series of five will fit 95% of the population to within a tolerance of ±2 mm in the maximum dimension.

Kinetic analyses of elbow flexion-extension in an attempt to define an axis, have produced conflicting results. London, J. T. (Kinematics of the Elbow. J. Bone and Joint Surg., 63A: 529-535, April 1981) was the first to relate the axis to a fixed reference line and showed that the joint moved as a uniaxial articulation which passed through the centre of the arcs formed by the trochlear sulcus and capitellum. He noted that the axis changed at the extremes of flexion-extension.

Fischer, O. (Zur Kinematik der Gelenke vom Typus humeroradial Gelenkes. Abh. d Math-phys. Cl. sk. ksachs, Ges., 32: 3-77, 1909), using Reuleaux's technique (Reuleaux, F.: The Kinematics of Machinery: Outlines of Theory of Mechanics (Translated and Edited by Kennedy, A. B. W.), New York, Dover, 56-80, 1963), found a locus of instant centres of elbow flexion-extension two to three millimetres wide near the centre of the trochlea. Using the same technique, Ewald, F. C. (Total Elbow Replacement. Orthop. S=Clin. North Amer., 6: 685-696, 1975) found constantly changing centres during flexion-extension. Andrews, J. G. and Chao, E. Y. (A General Method for Accurate Kinematic Analyses of Biomechanical Systems in Motion. J. Bone and Joint Surg., 54A: 1118, July 1972) found the instant centre of rotation at the midpoint of the perpendicular between consecutive screw axes. Using Taylor and Blaschke's technique (Taylor, C. L. and Blaschke, A. C.: A Method for Kinematic Analysis of Motions of Shoulder, Arm and Hand Complex. Ann. New York Acad. Sci., 51: 1251-1265, 1948-1951), Morrey and Chao (Morrey, B. F. and Chao, E. Y.: Passive Motion of the Elbow Joint: A Biomechanical Analysis. J. Bone and Joint Surg., 58A: 501-508, June 1976) also obtained a locus of instant centres near the centre of the trochlea. Schlein (Schlein, A. P.: Semiconstrained Total Elbow Arthroplasty. Clin. Orthop., 121: 222-229, 1976) located the axis of flexion-extension anterior to the midline of the humerus.

Knowledge of the exact location of the instant centres in flexion-extension is require for optimal placement of an elbow prosthesis to reduce the risk of loosening. In the above studies, however, the instant centres of elbow flexion-extension were not described with sufficient accuracy to be of practical use in the placement of a total elbow prosthesis during surgery.

A second aspect of elbow geometry is the "carrying angle". This angle is made by the intersection of longitudinal axes of the humerus and forearm in the frontal plane in the extended position. It has been measured and its variation in flexion debated. There are, however, relatively few reports on the effects of surface geometry in relation to the carrying angle.

OBJECT OF INVENTION

Having determined all of the above, it becomes an object of the present invention to provide an elbow prosthesis, or standardized series of prostheses, of the resurfacing type which replicate as far as possible the shape of a natural humerus or ulna.

BRIEF STATEMENT OF INVENTION

By one aspect of this invention there is provided an elbow prosthesis comprising a humeral component having an elongate bio-compatible member substantially C-shaped in cross section so as to provide concave and convex surfaces; the concave surface having a centroidal longitudinal axis and sized for close abutting relationship with a convexly prepared end of a distal humerus, said component including a plurality of contiguous highly polished convex metal surfaces replicating substantially exactly natural trochlea and capitellar articulatory surfaces of said humerus; said metal surfaces being definable, except for a trochlear flange thereof, by a longitudinal series of contiguous portions, the cross section of each of said portions being a segment of a circle the centres of which lie along a straight centroidal line which is coaxial with said centroidal longitudinal axis, and including: (i) a trochlear portion having a maximum diameter of between 24 and 32 mm adjacent the medial end thereof and a minimum trochlear diameter of between 14 and 20 mm at a point located centrally in the trochlear portion; (ii) a spherical capitellar portion with a diameter of between 19 and 24 mm which smoothly intersects with said trochlear portion adjacent the trochlear flange; said component being further defined by having a total length of between 45 and 50 mm, the length of the trochlear portion being between 21.3 and 26.3 mm, measured from the medial end thereof and the length of the capitellar portion being 15.5 and 19.1 mm, measured from the lateral end thereof.

BRIEF DESCRIPTION OF DRAWINGS

FIGS. 13 A–C are computer sketches of ulna sections.

DETAILED DESCRIPTION OF PREFERRED EMBODIMENTS (a) Analysis of anatomical shape of the elbow articulatory joint surfaces In an initial study four cadaveric elbows, two from males and two from females were investigated using the slicing technique described hereinafter. From this study sufficient data was generated for shape and alignment definition. Additional detailed linear dimensional studies of a large sample of elbows by the present inventors were combined with the small three dimensional surface study sample described herein, in order to provide a statistically meaningful sizing method. The major dimension coincided with those of prior workers. From these statistical results it has been possible to develop a series of three or five standard elbow sizes as set forth in Table 1 below.

TABLE 1

| | characteristic sizes of humeral surface for 95% coverage of population (mm) | | | | | | |
|---|---|---|---|---|---|---|---|
| | CA | ED | F | DIAM 1 | DIAM 2 | DIAM 5 | W |
| Three sizes | 25.9 | 18.9 | 68.1 | 29.8 | 18.1 | 23.4 | 48.7 |
| | 23.8 | 17.4 | 62.6 | 27.3 | 16.6 | 21.5 | 44.7 |
| | 21.7 | 15.8 | 57.1 | 24.9 | 15.2 | 19.6 | 40.8 |
| Five sizes | 26.3 | 19.1 | 69.2 | 30.2 | 18.4 | 23.7 | 49.4 |
| | 25.1 | 18.3 | 65.9 | 28.8 | 17.5 | 22.6 | 47.1 |
| | 23.8 | 17.4 | 62.6 | 27.3 | 16.6 | 21.5 | 44.7 |
| | 22.6 | 16.4 | 59.3 | 25.9 | 15.8 | 20.3 | 42.4 |
| | 21.3 | 15.5 | 56.0 | 24.5 | 14.9 | 19.2 | 40.0 |

A slicing method was devised to reconstruct three-dimensionally the anatomical shape of the elbow articulating joint surfaces.

Four embalmed human cadaver elbows were obtained. First, the soft tissues were carefully dissected from the elbow joint avoiding damage to the articular cartilage.

Next a coordinate system was used to standardize the position of each specimen. The x-axis is defined as the transepicondylar line (TEL). The y-axis is the long axis of the humerus and the z-axis is at the intersection of the x—and y-axes and perpendicular to the x-y plane. The distal humerus and proximal ulna were individually mounted and positioned by a precise alignment frame in an aluminum casing containing fiberglass reinforced resin. The medial and lateral epicondyles were held by pins in the frame to fix the TEL for the distal humerus.

The ulnae were positioned by means of a humeral prosthesis which provided alignment. The ulnae were allowed to find their natural seating position on this prosthetic base, and were then fixed in a polyester block similar to the humeral process.

Each mounted humeral specimen was clamped securely onto the bone milling machine, with the lateral epicondyl facing toward the operator. The transepicondylar line (TEL) remained perpendicular as the specimen was moved on a precise track past a revolving milling cutter. Each cut removed 0.76 mm thickness of bone from the specimen. The exposed surface, was photographed onto 35 mm standard colour film using a camera mounted on the milling machine. The surface of the cartilage was stained with alizirin red to give sharp definition. External reference lines parallel to the y- and z-axes of the specimen and a frame counter were used as a background to identify each cut surface. The mounted specimen and camera were advanced 0.76 mm between each cut to keep the distance constant for all photographs. A similar technique was used for the ulnae, with its lateral surface toward the operator.

Geometric Analysis

After development, the films were analyzed in a Bell & Howell Mark II Film Analyzer. Each frame showing the cut bone and cartilage was projected onto the surface of a Hi-Pad Digitizer (Houston Instruments). The cartilagenous outline of the humerus or ulna, the y- and z-axes, and the point representing the TEL were digitized using a cursor and plotted. Approximately one hundred points were recorded for each surface outline and these data fed into a desk-top Hewlett Packard computer. The stored data were then used to reconstruct the original surfaces for analysis of its anatomical shape.

When a geometric body is sectioned in an arbitrary direction, for example, a cylinder at 45 degrees with respect to its long axis, the outline of each section may or may not be a standard curve (circular, elliptical etc.). However after the data of all slices is combined, the true geometry of the body can be reconstructed and studied for special features and alignment. The validity of this statement, the precision and the accuracy of our technique has been established by slicing a wooden cylinder with a spherical end, and by slicing an intact (articulated) elbow obliquely.

The distal humerus appears symmetric about an axis which is at an angle to the TEL in the Coronal plane. If this were true, each slice perpendicular to that axis would have a common center and appear circular with the exception of the lateral flange of the trochlear. The assumption of circularity of the section outlines was tested by selecting coordinates of three data points located at one third distance from each other along the profile of each slice. A circle was fitted through these points and its radius as well as centre was determined. By repeating this for all the data of each slice, the variation in radius and centre location for each set of three points was found. If centres cluster around a mean value, the slice is circular with the mean value as centre. The line extended through the epicondyles of the humerus is referred to as the transepicondylar line (TEL) and is used as a reference. The line could be chosen arbitrarily. The TEL, however, is well defined anatomically and a consistent feature. Using the TEL does not pre-judge the outcome of the slicing.

Figure 1:
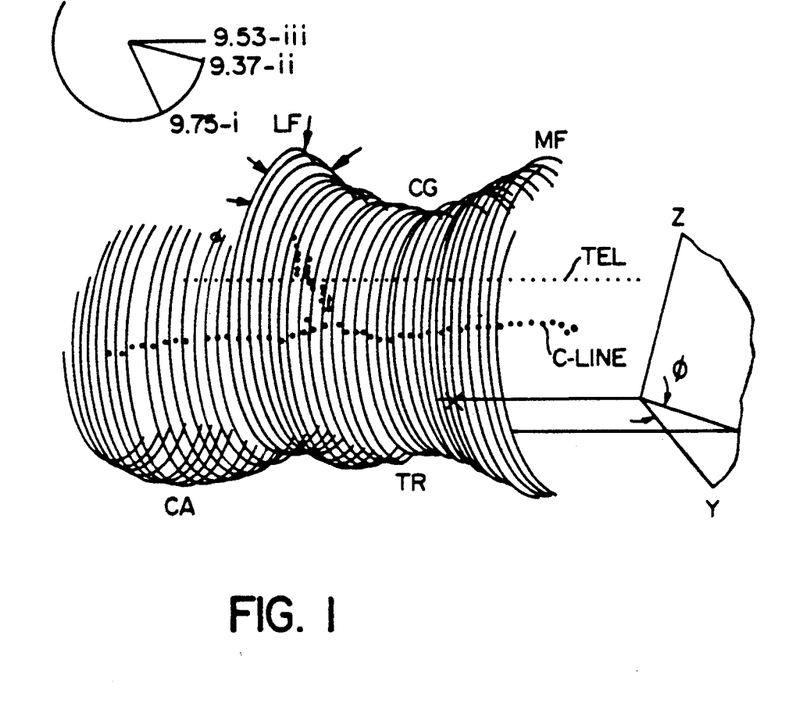
FIG. 1 is a computer composite of 50 slices through a distal humerus.

FIG. 1 illustrates a computer composite of 50 slices combined to represent the joint surface of the distal humerus. Each slice is made up of digitized coordinates. These coordinates subsequently were divided into three equal sections, starting at one end of the curve. One point was chosen from each section and a circle was fitted through each set of three points. The radius of each circle was calculated, and this process was repeated, until all coordinate points had been represented. The minimum, maximum and average radii were plotted, for each digitized slice, as shown in FIG. 1. The surface of each slice appeared to be very close to an arc of a circle, judged from the small deviations of centres, found for each set of radii. The best fit line through the centres of each slice form the centroidal axis of the humeral articulating surface (C-line). The slices deviate only from the circular pattern at the lateral flange of the trochlea (Lf). The slices through Lf consist of two circular sections with distinct centres, one on the C-line, and one at a particular distance from this line.

Figure 2:
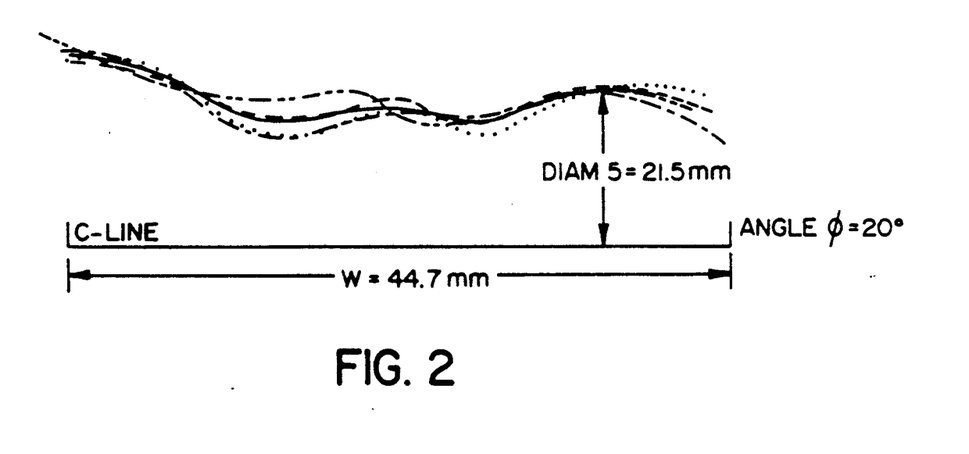
FIG. 2 is a graph of 4 different humeral outlines.

Computer aided sectioning with planes through the C-line will produce surface outlines of the joint at any required angular interval $\phi$, FIG. 1, which in turn can be used for templates in prototype joint and mould manufacturing. FIG. 2 shows four different elbow outlines, each outline at angle $\phi = 20°$. The outlines are normalized with respect to width W of the medium size out of the five sizes in Table 1 and the median diameter DIAM 5 also from Table 1. Each point $P_i$ of an outline has its radial distance to the C-line. The residual value R of the 4 elbows with respect to the average profile as shown by a solid line in FIG. 2 is given in Equation (1). This provides a measure of precision for shape and size.

$$R = \frac{1}{n} \sum_{j=1}^{n} \sqrt{\left[ \sum_{i=1}^{4} (P_i^2) - 4(\overline{P_j})^2 \right] / 3} \quad (1)$$

where
R = mean residual
n = number of data points
$P_i$ = radial distance from C-line
$\overline{P_j}$ = average radial distance to C-line Normalization with respect to W and with respect to one of the dimensions DIAM 5, DIAM 2, DIAM 1, T, E-D and C-A, at different angles $\phi$ was performed. The combination W and $D_5$ gave the least residual value. FIG. 2 therefore best represents the geometry and size combination.

Figure 3A:
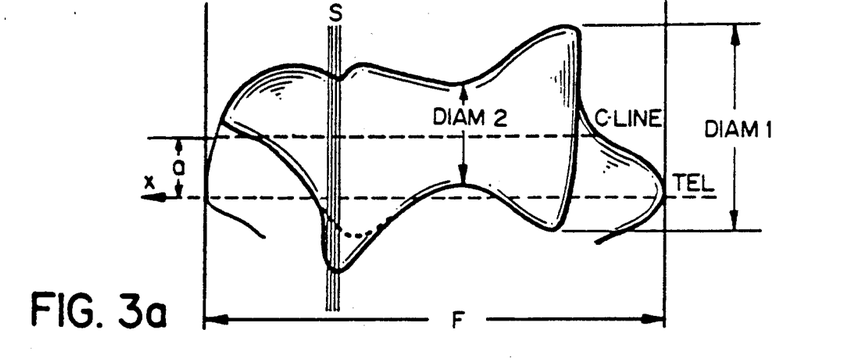
FIGS. 3a,b and c are sketches illustrating the surface shape of the distal humerus reconstructed from computer plots.
Figure 3B:
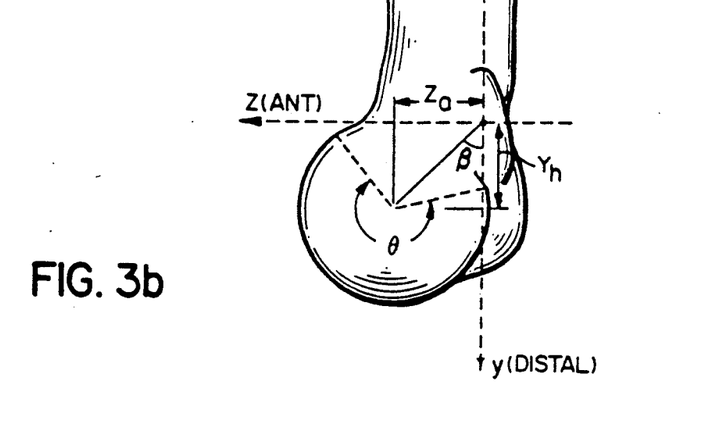
Figure 3C:
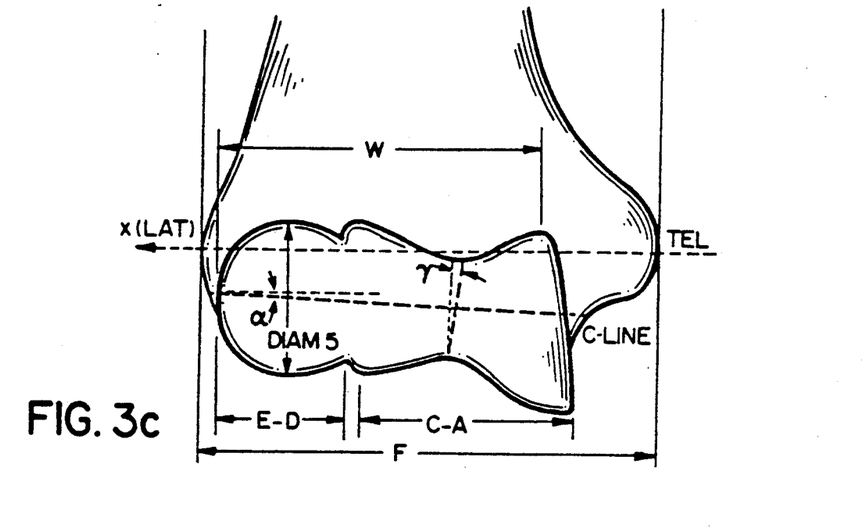

FIG. 3 represents the surface shape of the distal humerus reconstructed from computer plots. The C-line can be seen to run at an angle of $\alpha$, which is generally between about 1° and 10° and most often between 2° and 3°, with the TEL in the anterior-posterior view (negative z-direction), while both axes are parallel in the distal proximal view, (negative y-direction). This determines the articulating joint surface position in space at the distal end of the humerus. The centre of the medial part of the trochlea lies on a line that inclines at an angle $\beta$ with the long axis of the humerus, (y-axis). This angle is approximately 45°. The origin at the medial side of the C-line occurs at coordinates $Y_h$, $Z_a$. The angle $\gamma$ formed by the central groove of the trochlea and the line perpendicular to the C-line, determines together with $\alpha$, and ulnar anatomical features, the carrying angle, as hereinafter described.

Carrying Angle

Figures 11, 12:
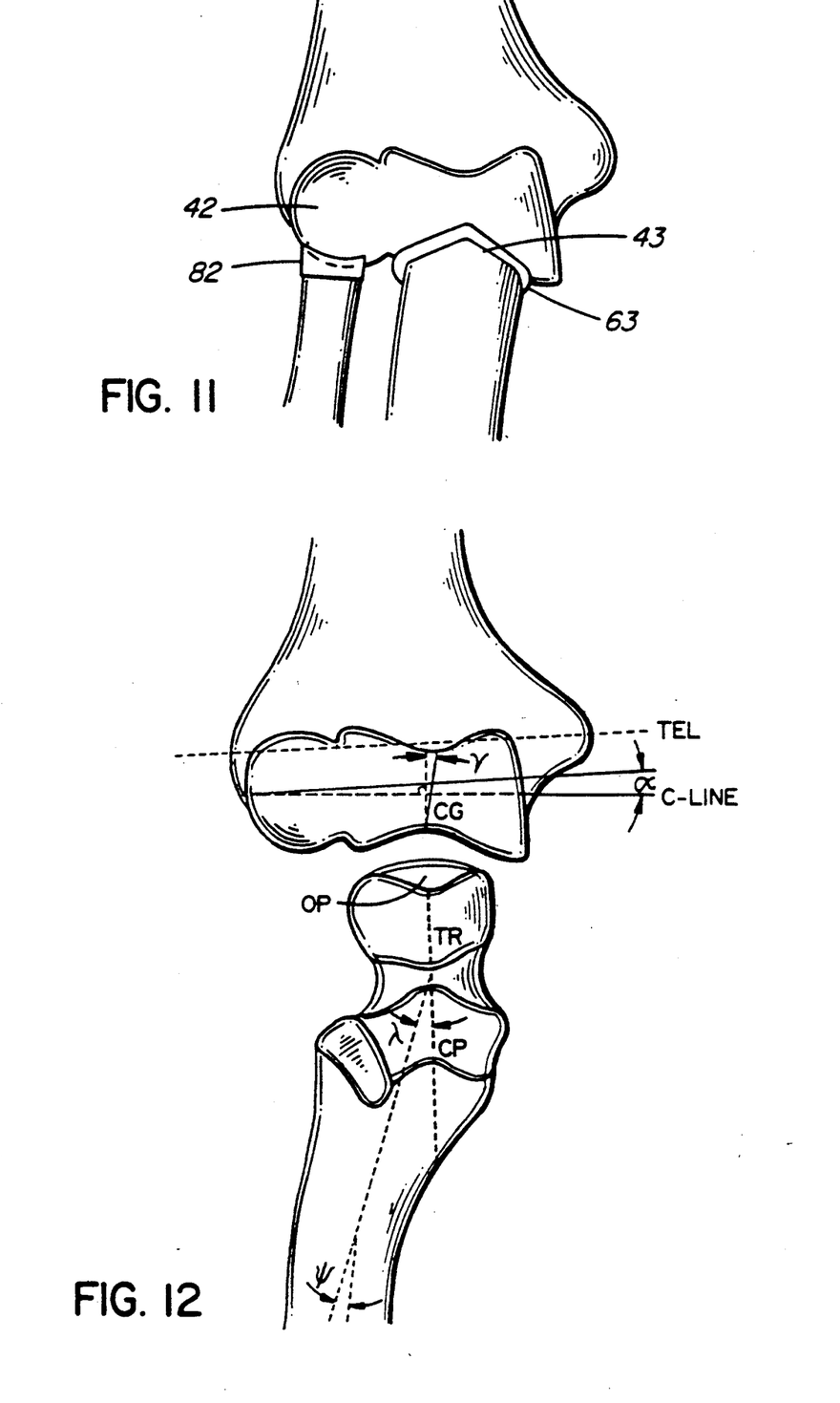
FIG. 11 is a sketch showing the cooperation of humeral, radial and ulna prostheses.
FIG. 12 is a sketch of a distal humerus and proximal ulna; illustrating the carrying angle.

The angles $\psi$, $\lambda$, $\alpha$ and $\gamma$ are four components of the carrying angle in the distal humerus and proximal ulna (FIG. 12, Table 2).

TABLE 2

| specimen & sex | Carrying Angle degree | | | | |
|---|---|---|---|---|---|
| | distal humerus | | proximal ulna | | carrying angle |
| | $\alpha$ | $\gamma$ | $\lambda$ | $\psi$ | $\alpha + \lambda + \psi$ |
| 1F | 2.5 | 8.0 | 21.0 | −6.0 | 17.5 |
| 2F | 2.5 | 5.0 | 14.0 | −7.0 | 9.5 |
| 3M | 2.5 | 2.0 | 7.0 | −7.0 | 2.5 |
| 4M | 2.5 | 3.0 | 17.0 | −12.0 | 7.5 |

$\alpha$ Angle between C-line and TEL,
$\gamma$ Inclination of central groove (cg)
$\lambda$ Angle between trochlear notch (tn) and proximal shaft of ulna.
$\psi$ Reverse angulation of shaft of ulna.

The angles ψ and λ in the ulna are formed by the shaft of the ulna with the plane of the trochlear ridge (tr). However, angle γ exists in the frontal plane and cannot, therefore, contribute to the carrying angle during early flexion. In extension and early flexion, the carrying angle is composed of the angles α, λ and ψ. The carrying angle in extension and early flexion was found to be 9.5 and 17.5 degrees in the two female and 2.5 and 7.5 degrees in the two male specimens (Table 3). With further flexion, the carrying angle should change as the coronoid process tracks along the anterior part of the central groove of the trochlea. As this happens the forearm rotates internally.

Statistical Analysis of Elbow Dimensions

On the distal humerus, of FIG. 3, seven dimensions F, W, ED, CA, DIAM 1,2 and 5 were chosen for statistical analysis of the joint. The width F or epicondylar distance can be palpated and measured by a constant pressure vernier caliper. This dimension, together with a standardized radiograph of the elbow joint will enable a surgeon to preoperatively determine the size of the required prosthesis. To quantify the variation of these 7 dimensions, a sampling of 59 dry bones were measured. These samples had no apparent deformities, and were obtained at random. It is not known if there were left and right pairs in this sample. There are no differences in left or right elbows of one person, a fact that has been shown by other studies, therefore entering the data of a pair of elbows is basically the same as entering two identical dimensional values to the data bank.

Figure 4:
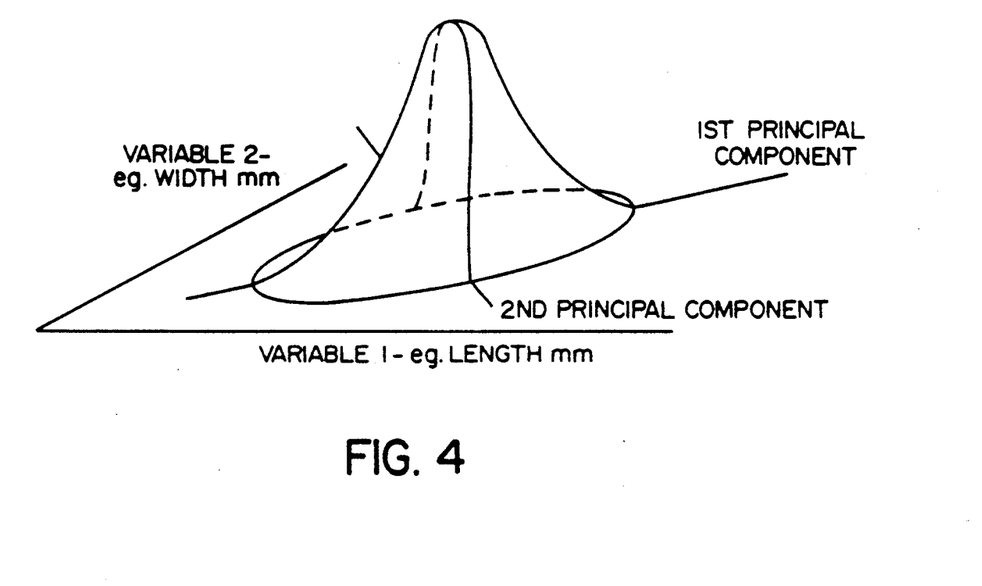
FIG. 4 is a probability curve of dimensional variables.

Each one of the seven dimensional variables was tested by determining if it fitted a normal distribution by producing standard normality plots. Each variable appeared normal on these plots and this enabled the use of a multivariate normal probability distribution model. This model lends itself for analysis by principal component (PC). Principal components are linear combinations of the 7 variables with special properties in terms of variance. This will be illustrated by using 2 variables (e.g.) the length and width of a rectangular object), each dimension is considered to be normally distributed. The probability of occurrence would look like a surface shape shown in FIG. 4. The first principal component has the largest variance while the second has the least variance. One would hope to find that the data varies in such a manner that the first principal component contains the bulk of the variance. This would mean for the 2 variable example that the probability surface is narrow and long at its base. If variable 1 (length) and variable 2 (width) were strongly correlated, the elliptical base reduces to a line. The probability surface would then be a normally distributed "bell-curve" with the first principal component as base line. This visual representation breaks down beyond 2 variables but the analysis of 3 or more variables is the same. For 7 variables, the principal components were ranked 1 to 7. The analysis shown that the first PC contained 70% of the variance, the second 13%, the third 6% with the remaining principal components making up the rest.

Figure 5:
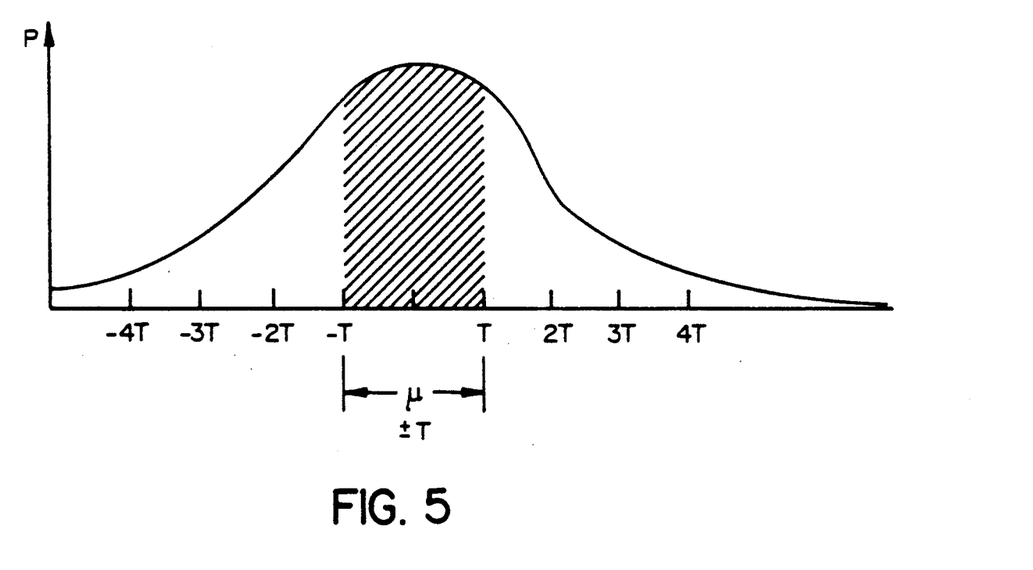
FIG. 5 is a graph illustrating a normal distribution curve.

Having established that the first PC of the 7 elbow variables accounted for 70% of the variance one can represent this PC as a normally distributed value, FIG. 5. The area under the curve at different intervals indicates the probability that those PC values occur in the population. The interval width is twice the tolerance that can be accommodated by a patient receiving a resurfacing prosthesis. The middle interval μ±T has the highest probability of occurrence. If T is chosen relatively large then a few intervals such as −3T to −T, −T to +T and +T to +3T could cover a large percentage of all random occurrences in patients. By varying the tolerance T on the first PC and by choosing a fixed series of intervals or sizes, the proportion of the population that will be covered can be calculated from Equation (2).

$$\text{Proportion covered} = 1 - 2]1 - F\left(\frac{nT}{\sigma}\right) \quad (2)$$

Figure 6:
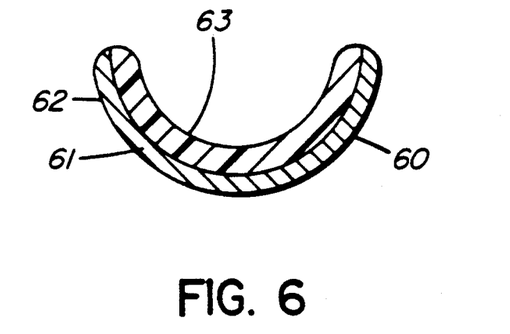
FIG. 6 is a side sectional view of an ulna prosthesis.

$F$ = statistical function to be found in the literature $\sigma$ = standard deviation in dry bone samples in mm $T$ = tolerance in mm $n$ = number of data points By plotting the proportion covered in the population against the tolerance T the graph in FIG. 6 is created. This graph is a useful tool for design and clinical decision making.

From the values for the first PC, the values of the second PC and all others in descending order of importance follow mathematically. By transforming the ranked seven PC's back to actual elbow dimensions, the set of sizes shown in Table 1 has been established for 95% coverage, However, each one of the seven dimensions will not necessarily represent 95% of all persons, as can be observed in Table 3.

TABLE 3

Tolerances in mm and Percentages Covered for Each Dimension Obtained From the First Principal Component Analysis (PC)

| DIMENSIONS | 3 SIZES | 5 SIZES | % COVERED |
|---|---|---|---|
| C-A | 1.1 | .7 | 90 |
| E-D | .7 | .4 | 87 |
| F | 2.5 | 1.5 | 93 |
| DIAM 1 | 1.5 | .9 | 90 |
| DIAM 2 | .7 | .4 | 71 |
| DIAM 5 | .9 | .6 | 86 |
| W | 2.2 | 1.3 | 94 |

As can be noted from Table 3, the DIAM 2 covers much less of the population than in the case for the other dimensions. This reveals that DIAM 2 is not linearly related to the other variables. Simple sizing by equal expansion or shrinking of all elbow dimensions is therefore less accurate for DIAM 2.

An alternative method of sizing would be to take the first PC and the second PC simultaneously into account, and establish two-dimensional intervals as bases for the probability that values fall within this interval. then divide the sizes so that coverage for DIAM 2 is increased. However, because the sizing is now based on 2 PC's, sizes are no longer ranked from biggest to lowest for all dimensions. For example, if ranked by width W, from largest width to smallest, DIAM 2 would not obey that ranking. While sizes would cover the population better as far as each one of the seven dimensions is concerned, the choice of size by the surgeon cannot be based on one preoperative measurement such as the width. Rather all seven dimensions must be preoperatively assessed or measured during surgery. This is complicated, and the sizing along one PC, Table 1, is considered to offer the best compromise.

(b) Insertion of humeral prostheses

In order to insert a humeral prosthesis 42 of the present invention, fabricated from a conventional surgical cobalt-chrome alloy such as "Vitallium" ®, other stainless steel or titanium or, non-toxic other biocompatiable material such as a ceramic material and having an outer surface shape defined as above, it is necessary to make incisions from the medial and lateral sides of the elbow to provide access to the trochlea and capitellum for trimming to a shape which will match the inner surface shape of the prosthesis, and to provide a relatively tight interference fit therewith. The inner surface of the prosthesis is cast or machined to a concave cylindrical form having a longitudinal axis which is substantially coincident with the centroidal axis (C-line) of the articulating surface, so that in cross section the interior of the prosthesis is substantially C-shaped. The concave surface is preferably coated with a porous metal layer which promotes bone ingrowth and aids fixation of the prosthesis to the bone in what is now recognized as a conventional technique.

The centroidal line is determined by selecting the centre of the medial flange of the trochlea and the centre of the lateral surface of the capitellum. the line between these points is the centroidal line around which the surface bone and cartilage of the trochlea and capitellum is removed at a defined distance or arc from the line. This centroidal axis in line with which the component is positioned or inserted is at an angle of 1°–10°, in the coronal plane to the TEL.

A jig or guide device is required to (a) hold the patients elbow in a preselected position for cutting, (b) provide a rigid base for the cutting tool and (c) provide a device for guiding the cutting tool in making accurate cuts. The cutting tool may be a saw, router, burr or other conventional bone cutting device. One such device is described in detail in applicants commonly assigned parent application Ser. No. 507,378 filed June 24, 1983 and an alternative thereto is described in detail in applicants commonly assigned continuation-in-part application Ser. No. 730,931 filed May 6, 1985 and now U.S. Pat. No. 4,624,250 issued Nov. 25, 1986.

(c) Ulna Prosthesis

Figure 13A:
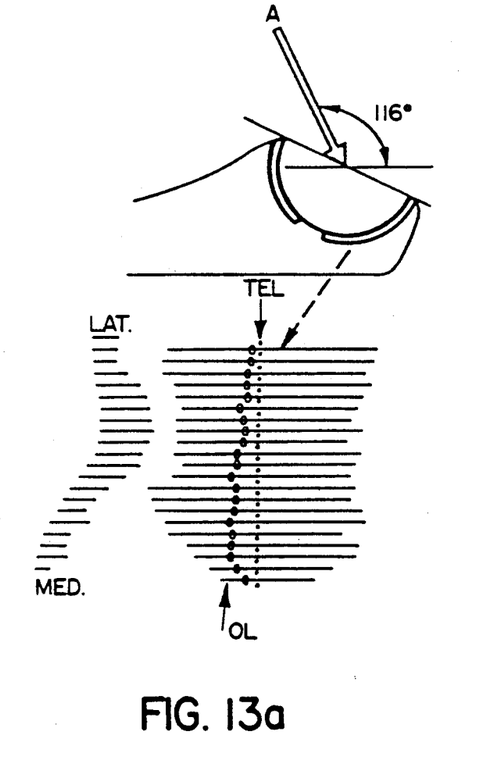
Figure 13B:
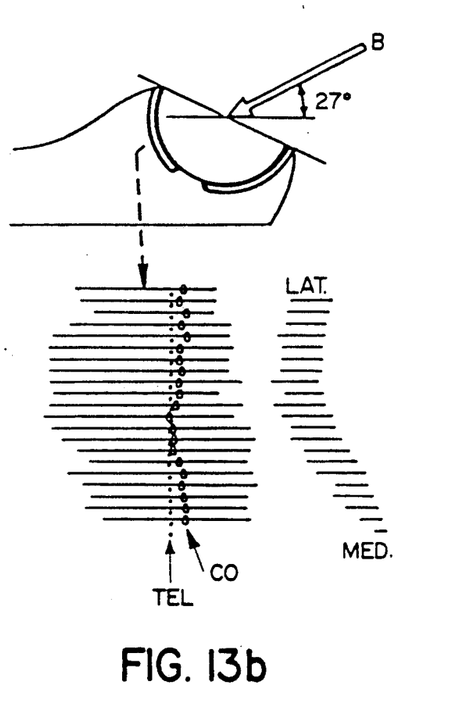
Figure 13C:
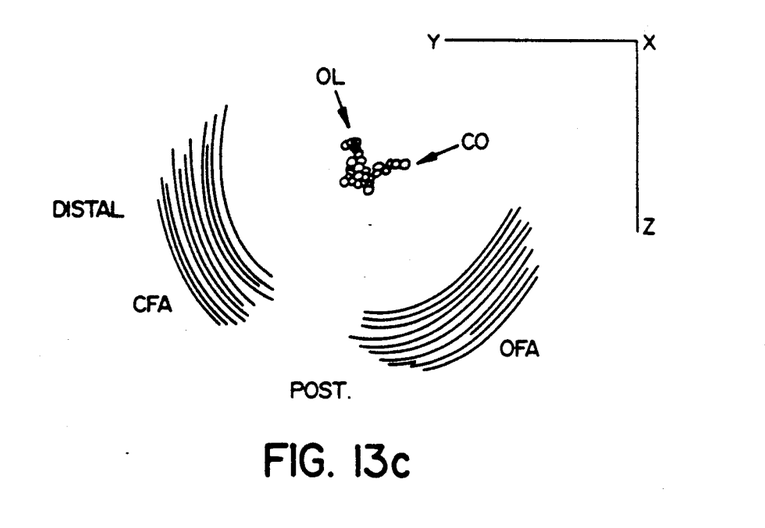

The results from all four proximal ulnae were almost identical to each other (FIG. 13c). The centres calculated from each set of three points on the outline of the cut surfaces of the olecranon and coronoid facets were clustered into two groups about the TEL except for a few centres from the lateral and medial limits of the cut surfaces which deviated from each cluster. The centres obtained from the curve of the olecranon facet deviated in the direction indicated by the arrow OL, at the lateral and medial limits, and those from the curve of the coronoid facet deviated in the direction indicated by the arrow CO. Small clearances existed between the trochlear flanges and both the olecranon and coronoid facets at their outer limits.

The centres of curvature were generally collinear for the olecranon facet when viewed from the direction indicated by the arrow A, (FIG. 13), and for the coronoid facet when viewed from the direction indicated by the arrow B (FIG. 13).

The extent of cartilagenous cover of the trochlea when viewed from the lateral side is the arc subtended by angle $\theta$, (FIG. 3b). The mean angle was 250 degrees at the lateral flange, 245 degrees at the central groove and 216 degrees at the medial flange (Table 3).

The coronoid and olecranon articulating facets were distinct from each other and linked by the noncartilage-covered incisura trochlearis. Cartilage extended over the coronoid facet ($\sigma_{CO}$) in an arc with a mean value of 79 degrees. The extend of cover of the olecranon facet ($\sigma_{OL}$) was 76 degrees. The incisura was an arc of 25 degrees. (Table 3).

The articulation between the central groove of the trochlea and the trochlear notch of the ulna was estimated. The cartilagenous surfaces would appear to contact each other fully between 55 to 116 degrees of elbow flexion. At full extension, part of the surface of the olecranon facet appears to lose contact with the central groove of the trochlea. Similarly at the limit of flexion, the coronoid facet would tend to lose contact with the trochlear groove.

It appears from the extent of cartilagenous cover of the distal humerus and proximal ulna that the central groove of the trochlea articulates mainly with the coronoid facet of the ulna in extension and early flexion and mainly with the olecranon facet in terminal flexion of the elbow. These observations suggest the possibility of two distinct bearing surfaces at the humero-ulnar articulation; one mainly for early flexion and the other mainly for terminal flexion.

The medial to lateral stability of the elbow joint is provided mainly by the capsule, the collateral ligaments and bony structures. While forces are generated on both the humero-radial and humero-ulnar articulations of the elbow, they are generated mainly at the latter.

The medial flange of the trochlea is of larger diameter than the lateral flange. In extension and early flexion medial stability (adduction movement) is provided largely by the medial flange and the lateral collateral ligament. Lateral stability (abduction movement) is provided by the lateral flange of the trochlea, the capitulo-radial articulation and medial collateral ligament. With increasing flexion and at terminal flexion of the elbow, the enlargement noted herein, at the posterior part of the lateral flange of the trochlea, could be an important stabilizer of abduction movements.

Two distinct articular facets in the ulna (olecranon and coronoid) are present in 64% of elbows joined by cartilage free incisura. In other elbows, the incisura is covered by cartilage to a greater or lesser extent. The behavior of these facets in early and late flexion referred to above and the observations herein of non-coincident centres of curvature suggests a slight "sloppiness" of fit between ulna and humerus.

Figure 7:
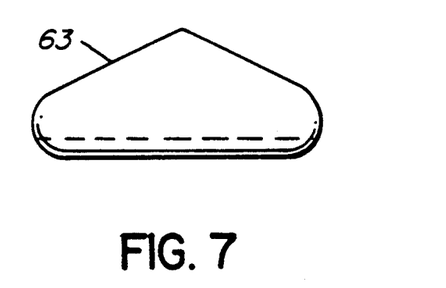
FIG. 7 is an end view of the prosthesis of FIG. 6
Figure 8:
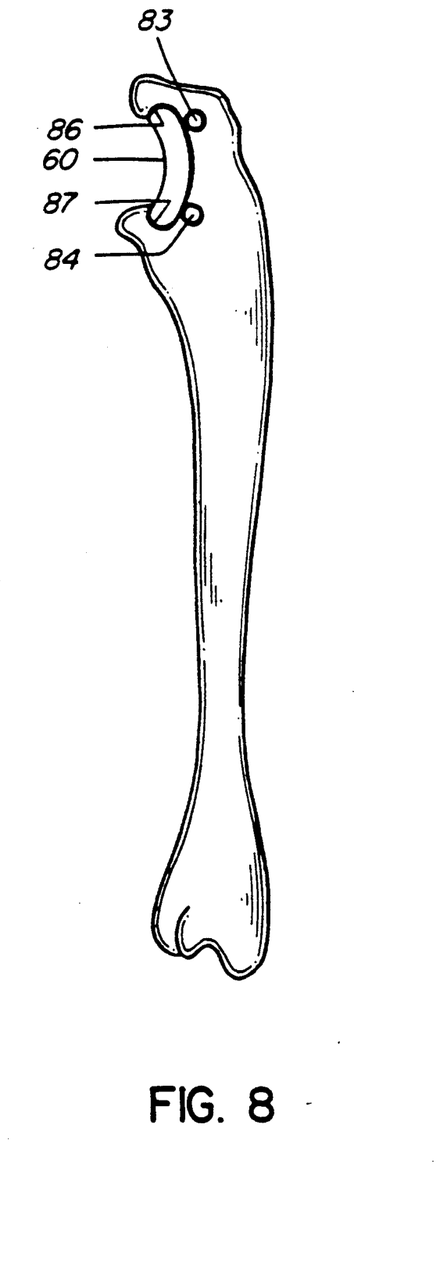
FIG. 8 is a side view of an alternative ulna prosthesis in situ.

The above considerations permit the production of a complementary proximal ulna prosthetic element 60, shown in FIGS. 6 and 7 which comprises a curved bio-compatible material such as stainless steel shell 61 preferably fabricated in Vitallium ® or similar alloy having a porous metal layer (as previously described) 62, or a ceramic material with a porous surface larger, on the convex surface thereof and a high density polyethylene (HDPE) layer 63 on the concave surface (in the lateral direction, FIG. 7) thereof. The HDPE layer 63 is convexly and concavely contoured (medial view, FIG. 6) to complement the concave/convex portion 43 of humeral prosthesis 42, and to articulate smoothly therewith. The HDPE layer 63 is arranged to snap fit into the steel backing shell 61, for easy installation, removal and replacement as necessary. Alternatively layer 63 may be permanently fitted into shell 61. The shell 61 is arranged to be a close friction fit in the cavity cut in the ulna therefore and is prevented from rotating by means of undercutting 86, 87 on the bony structure of the ulna, as shown in FIG. 8. If desired, for extra insurance against rotation, rods 83, 84 may be welded onto shell 61 and complementary holes provided in the ulna, as shown in FIG. 8, or wires (not shown) may be provided to secure shell 61 into the aforesaid holes.

(d) Insertion of Ulna Prosthesis

Figure 9:
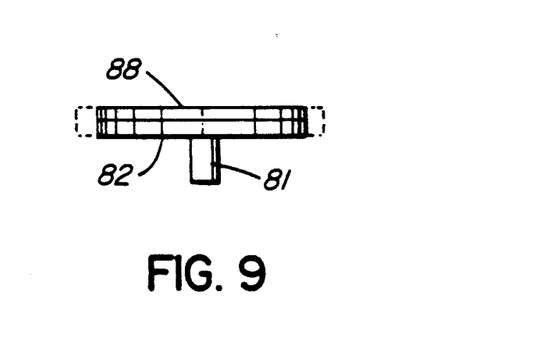
FIG. 9 is a side view of a radial prosthesis.
Figure 10:
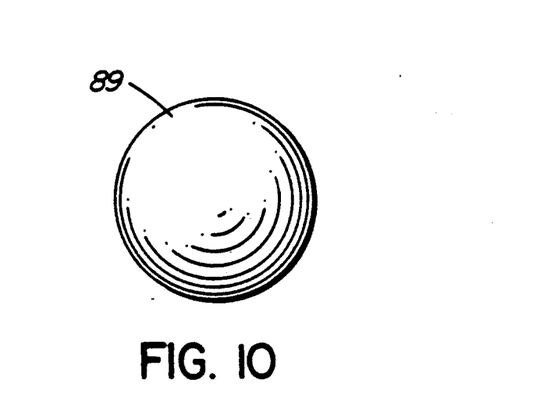
FIG. 10 is a plan view of the prosthesis of FIG. 9.

In order to insert the prosthesis, the olecranon 86 and coronoid 87 facets are trimmed to a shape to receive the convex porous metal coated surface of the prosthesis 60. Preferably, the elbow is held in one of the jigs described in the aforementioned copending applications, so that both the humeral and ulna cuts can be made while the humerus and ulna are clamped in the same positions relative to each other such that the humeral and ulna arcuate cuts can be made from the same centre, using appropriately sized cutting guides. cl (e) Radial Prosthesis The entire end of the radius is normally removed replaced by a prosthetic tip, as shown in FIGS. 9 and 10. The radial prosthesis comprises a fabricated in a stainless steel or other bio-compatible material, stem 81 with an enlarged circular end 82 into which or around which a thermo-plastic head 88 is a snap fit. The bearing surface 89 of head 88 is slightly concavely dished to match the curvature portion of the humeral prosthesis. The stem surfaces and the exposed underside of the end 82 are preferably porous coated, similar to that described above. The thickness of plastic head 88 which is preferably but not essentially fabricated from high density polyethylene, may be varied, as appropriate to take up or reduce the joint space as determined by the surgeon during insertion.

It will be appreciated that, unlike prosthesis of the prior art which are at best rough approximations to the natural articulating surfaces, the humeral component herein is so close in shape to the natural articulating surface that it alone can be inserted into an elbow joint for articulation with the natural ulna and radius. It is not necessary to replace the ulna and radius with a prosthesis unless there is a medical or surgical reson for so doing, such as deterioration of the articulating surface due to rhuematoid arthritis. In many trauma cases, such as motorcycle accidents, the humerus is badly damaged but the ulna and radius remain undamaged.

We claim:

1. An elbow prosthesis comprising a humeral component for insertion into a human elbow to replace the natural surface of the humerus, the surface of said humerus being spaced, in the coronal plane, from a transepicondylar line which extends between opposed epicondyles of said humerus, said prosthesis having an elongate bio-compatible member substantially C-shaped in cross section so as to provide concave and convex surfaces; the concave surface having a centroidal longitudinal axis and sized for close abutting relationship with a convexly prepared distal end of said humerus, said component including a plurality of contiguous highly polished convex surfaces replicating substantially exactly natural trochlea and capitellar articulatory surfaces of said humerus; said surfaces being definable, except for a trochlear flange of a trochlear portion thereof, by a longitudinal series of contiguous portions, the cross section of each of said portions being a segment of a circle, the centers of which lie along a straight centroidal line which is coaxial with said centroidal longitudinal axis, said centroidal longitudinal axis lying at an angle between 1° and 10° to said transepicondylar line when inserted into said elbow as seen in the anterior-posterior view, and in parallel as seen in the distal proximal view.

2. A prosthesis as claimed in claim 1 and further including an ulna component designed for insertion from the medial side of the elbow to articulate with the trochlear surfaces of the humeral component and comprising a longitudinally extending bio-compatible element, substantially C-shaped in cross section so as to provide concave and convex surfaces for location, respectively, adjacent said trochlear surface and in close abutting relation with a concavely prepared proximal end of an ulna, and a thermoplastic element, releasably engageable with said concave surface of said bio-compatible element, and having a smooth concave surface contoured for articulation with said trochlear surface of said humeral component.

3. A prosthesis as claimed in claim 2 wherein said humeral component and said ulna bio-compatible element are metallic and said thermoplastics element is fabricated in high density polyethylene.

4. An elbow prosthesis as claimed in claim 3 wherein said concave surface of the humeral component and the convex surface of said ulna element are each provided with a porous coating so as to promote bone in-growth.

5. An elbow prosthesis as claimed in claim 2 further including a radial component comprising a circular bio-compatible material disc portion having opposed planar surfaces and a stem extending axially from one said planar surface thereof arranged to provide engaging means between said one planar surface and a complementary prepared proximal end of a radial bone in abutting relation thereto and a thermoplastics element secured to the other planar surface of said bio-compatible disc portion; said thermoplastics element having a slightly concave portion complementary to the convex surface of said humeral component.

6. An elbow prosthesis as claimed in claim 5 wherein said bio-compatible portion of said radial component is fabricated in stainless steel and the radial thermoplastics element is fabricated from high density polyethylene.

7. An elbow prosthesis as claimed in claim 6 wherein said stem and said one planar surface of the bio-compatible radial portion are coated with a porous coating so as to promote bone in-growth.

8. An ulna component as claimed in claim 1 wherein said convex surface of said bio-compatible element is porous metal coated.

9. A method for inserting a humeral prosthesis into a human elbow comprising the steps of effecting incisions on the medial and lateral sides of the elbow, trimming the trochlear and capitellar surfaces of the humerus to provide a regular convex surface having a centroidal longitudinal axis which lies at an angle between 1° and 10° to a line extending between the epicondyls of said humerus in the coronal plane, and mounting on said convex surface a humeral prosthesis having a convex articulating surface, and a complementary concave surface to said regular convex surface, said articulating surface and said complementary concave surface having coincidental longitudinal centroidal axes.

10. An elbow prothesis comprising a humeral component for insertion into a human elbow to replace the natural surface of the humerus, the surface of said humerus being spaced, in the coronal plane, from a transdepicondylar line which extends between opposed epicondyls of said humerus, said prothesis having an elongate bio-compatible member substantially C-shaped in cross section so as to provide concave and convex surfaces; the concave surface having a centroidal longitudinal axis and sized for close abutting relationship with a convexly prepared distal end of said humerus, said component including a plurality of contiguous highly polished convex surfaces replicating substantially exactly natural trochlea and capitellar articulatory surfaces of said humerus; said surfaces being definable, except for a trochlear flange of a trochlear portion thereof, by a longitudinal series of contiguous portions, the cross section of each of said portions being a segment of a circle, the centers of which lie along a straight centroidal line which is coaxial with said centroidal longitudinal axis; said convex surfaces being further defined by an angle of inclination of a central groove formed by said trochlear portion and a line perpendicular to the straight centroidal line, said angle ranging from 2.0° to 8.0°, said trochlear portion having a maximum diameter of between 24 and 32 mm adjacent the medial end thereof and a minimum trochlear diameter of between 14 and 20 mm at a point located centrally in the trochlear portion wherein the center of a medial part of said trochlear portion lies on a line which inclines at an angle of 45° with the long axis of the humerus; and further including a spherical capitellar portion with a diameter of between 19 and 24 mm which smoothly intersects with said trochlear portion at an end opposite said trochlear flange; the length of the trochlear portion being between 21.3 and 26.3 mm, measured from the medial end thereof and the length of the capitellar portion being between 15.5 and 19.1 mm, measured from the lateral end thereof.

11. An elbow prothesis comprising a humeral component for insertion into a human elbow to replace the natural surface of the humerus, the surface of said humerus being spaced, in the coronal plane, from a transdepicondylar line which extends between opposed epicondyls of said humerus, said prothesis having an elongate bio-compatible member substantially C-shaped in cross section so as to provide concave and convex surfaces; the concave surface having a centroidal longitudinal axis and sized for close abutting relationship with a convexly prepared distal end of said humerus, said component including a plurality of contiguous highly polished convex surfaces replicating substantially exactly natural trochlea and capitellar articulatory surfaces of said humerus; said surfaces being definable, except for a trochlear flange of a trochlear portion thereof, by a longitudinal series of contiguous portions, the cross section of each of said portions being a segment of a circle, the centers of which lie along a straight centroidal line which is coaxial with said centroidal longitudinal axis; said centroidal longitudinal axis lying at an angle between 1° and 10° to said transepicondylar line when inserted into said elbow as seen in the anterior-posterior view, and in parallel as seen in the distal proximal view; said convex surfaces being further defined by an angle of inclination of a central groove formed by said trochlear portion and a line perpendicular to the straight centroidal line, said angle ranging from 2.0° to 8.0°, said trochlear flange bulging outside of said segments of said circle.

12. An elbow prothesis according to claim 11, wherein said trochlear flange has a maximum diameter of between 24 and 32 mm adjacent the medial end thereof and a minimum trochlear diameter of between 14 and 20 mm at a point located centrally in the trochlear portion wherein the center of a medial part of said trochlear portion lies on a line that inclines at an angle of 45° with the long axis of the humerus; and further including a spherical capitellar portion with a diameter of between 19 and 24 mm which smoothly intersects with said trochlear portion at an end opposite said trochlear flange; the length of the trochlear portion being between 21.3 and 26.3 mm, measured from the medial end thereof and the length of the capitellar portion being between 15.5 and 19.1 mm, measured from the lateral end thereof.

13. A prothesis as claimed in claim 11 and further including an ulna component designed for insertion from the medial side of the elbow to articulate with the trochlear surfaces of the humeral component; said ulna component comprising a longitudinally extending bio-compatible element, substantially C-shaped in cross section so as to provide concave and convex surfaces for location, respectively, adjacent said trochlear surface and in close abutting relation with a concavely prepared proximal end of an ulna, and a thermoplastic element, releasably engageable with said concave surface of said bio-compatible element, and having a smooth concave surface contoured for articulation with said trochlear surface of said humeral component.

14. A prothesis as claimed in claim 13, wherein said humeral component and said ulna bio-compatible element are metallic and said thermoplastic element is fabricated in high density polyethylene.

* * * * *